United States Patent
Björling

(10) Patent No.: US 7,725,189 B2
(45) Date of Patent: May 25, 2010

(54) METHOD, DEVICE, AND SYSTEM CONCERNING HEART STIMULATION

(75) Inventor: Anders Björling, Järfalla (SE)

(73) Assignee: St. Jude Medical AB, Jarfalla (SE)

( * ) Notice: Subject to any disclaimer, the term of this patent is extended or adjusted under 35 U.S.C. 154(b) by 633 days.

(21) Appl. No.: 11/660,771

(22) PCT Filed: Aug. 31, 2004

(86) PCT No.: PCT/SE2004/001252

§ 371 (c)(1),
(2), (4) Date: Feb. 21, 2007

(87) PCT Pub. No.: WO2006/025771

PCT Pub. Date: Mar. 9, 2006

(65) Prior Publication Data

US 2007/0255329 A1    Nov. 1, 2007

(51) Int. Cl.
*A61N 1/37* (2006.01)
(52) U.S. Cl. ........................................ 607/28
(58) Field of Classification Search ........................ None
See application file for complete search history.

(56) References Cited

U.S. PATENT DOCUMENTS

| 5,273,049 A | 12/1993 | Stenhaus et al. |
| 5,697,957 A | 12/1997 | Noren et al. |
| 6,473,650 B1 | 10/2002 | Larsson et al. |
| 2003/0050671 A1 | 3/2003 | Bradley |
| 2003/0083711 A1 | 5/2003 | Yonce et al. |

FOREIGN PATENT DOCUMENTS

| EP | 0 605 244 | 7/2001 |
| WO | WO 2004/078258 | 9/2004 |

*Primary Examiner*—Carl H. Layno
*Assistant Examiner*—Jon-Eric C. Morales
(74) *Attorney, Agent, or Firm*—Schiff Hardin LLP

(57) ABSTRACT

In a cardiac stimulation method, device and system, a capture verification condition is determined. For this purpose, a number of pacing pulses are delivered to a heart chamber and signals are sensed within a time window following each pacing pulse. The sensed signals are stored and categorized as representing capture or non-capture. Using the stored signals, a weight vector is determined, that assigns different weights for different parts of each sensed signal within the time window. The weight vector is used for calculating a weighted area within the time window. The capture verification condition is determined by identifying whether the weighted area, calculated with the weight vector, of a sensed signal within the time window is above or below a predetermined value.

28 Claims, 4 Drawing Sheets

METHOD, DEVICE, AND SYSTEM CONCERNING HEART STIMULATION

BACKGROUND OF THE INVENTION

1. Field of the Invention

The present invention relates to heart stimulating devices and systems. In particular to such devices and systems that have the ability to detect evoked responses to stimulation pulses delivered to the heart of a patient. The invention also concerns a method of determining a capture verification condition.

2. Description of the Prior Art

Several different devices for stimulating a heart are known. Such devices are able to deliver stimulation pulses to one or more of the different heart chambers: the left ventricle, the left atrium, the right ventricle and the right atrium. The devices can often be implanted in a patient. The devices are normally also able to sense the electrical activity of the heart.

In connection with such devices, it is known to detect the capture of the heart, i.e. to detect whether the heart actually reacts as intended to a delivered stimulation pulse. If the heart is not captured (i.e. loss of capture) it is possible to arrange the device to deliver a back-up pulse with a higher pulse energy than the first pulse. It is also possible to increase the pulse energy in future stimulation pulses if capture is not detected. In order to save battery it is important that the stimulation pulses are not delivered with an unnecessarily high energy. By varying the energy of the stimulation pulses and by detecting the capture it is possible to find a threshold value for the stimulation pulse energy. Based on the threshold value, a suitable stimulation pulse energy can be determined.

The detection of capture, i.e. the detection of an evoked response (ER), can be done in different manners. Normally an IEGM (intracardiac electrogram) signal is detected within a time window (ER window) following a delivered stimulation pulse. The determination whether the detected signal indicates a capture can be performed in different manners. It is for example known to use the maximum amplitude of the detected signal within the ER window. It is also known to use a slope or derivative (usually the maximum slope) of the detected signal within the ER window. A third known possibility is to detect an area by integrating the detected signal in the ER window.

The detection of capture involves different problems. One problem is the electrode-polarisation. The electrode-polarisation is a residual voltage that appears at the electrode used for the stimulation. In particular if the same electrode is used for emitting the stimulation pulse and for sensing the evoked response, the electrode-polarisation can make the detection difficult.

It is also known that the delivery of stimulation pulses and the detection of the IEGM can be done either with unipolar or bipolar stimulation and detection.

U.S. Pat. No. 6,473,650 describes an ER detector. The basis for the detection is the idea that the electrode polarisation depends on the stimulation pulse amplitude, while the ER signal does not depend on this amplitude. The sensed signal is sampled and the DC level determined before the delivery of the pulse is subtracted from each sample.

U.S. Pat. No. 5,697,957 describes the suppression of electrode-polarisation components when detecting ER. The sensed cardiac signal is added to either a differentiated or autocorrelated sensed cardiac signal and a difference is formed between the original sensed cardiac signal and the autocorrelated or differentiated signal, thereby extracting an ER component from the sensed cardiac signal.

U.S. Patent Application Publication No. 2003/0083711 describes ER detection by comparing the detected signal with template wave forms. The ER is classified as representing a type of capture if the ER waveform highly correlates with a certain template waveform.

Also U.S. Patent Application Publication No. 2003/0050671 describes ER detection that involves the correlation between a sensed signal and a template waveform. The document describes in particular a method of identifying fusion beats.

SUMMARY OF THE INVENTION

An object of the invention is to provide an improved method of determining a capture verification condition for a heart stimulating system. A further object is to provider a method wherein the capture verification condition obtained by the method can be used to distinguish capture from loss of capture with improved accuracy. Another object of the invention is to provide an implantable heart stimulating device including such an improved capture verification condition. Still another object is to provide a heart stimulating system including such a device.

The above objects concerning the method are achieved by a method of determining a capture verification condition for a heart stimulating system. The heart stimulating system has at least a control circuit, a pacing electrode and a first sensing electrode, the sensing electrode can be the same as or different from pacing electrode. The control circuit has a pacing circuit connected to the pacing electrode and sensing circuitry connected to the sensing electrode. The method includes the following steps:

positioning the pacing electrode so that the pacing electrode is able to deliver pacing pulses to a heart chamber, positioning said sensing electrode so that the sensing electrode is able to sense evoked responses in response to pacing pulses delivered by the pacing electrode, delivering a number of pacing pulses, via the pacing electrode, to the heart chamber, wherein the number of pacing pulses includes pulses which cause the heart chamber to capture and pulses which do not cause the heart chamber to capture, sensing signals from the sensing electrode within a time window following after each of the delivered pacing pulses and storing the sensed signals in a memory, categorizing the stored signals in a first group and a second group, the first group representing captured cases and the second group representing non-captured cases, based on the stored signals, determining a particular weight vector which assigns different weights for different parts of each sensed signal within the time window and which is to be used for calculating a weighted area within the time window, the particular weight vector being determined to cause when using the particular weight vector to calculate the weighted areas for the stored signals, the signals of the first group to be more easily distinguished from the signals in the second group than if the signals in the first and second groups were distinguished from each other by said area without assigning different weights for different parts of the sensed signal within said time window, and the capture verification condition being determined by whether the weighted area, calculated with said particular weight vector, of a sensed signal within said time window, is above or below a certain value.

It should be noted that the mentioned time window can also be called the ER window. This window can start, for example, somewhere between 0 ms and 30 ms after the delivery of a pacing pulse. The window can for example have a duration of between 10 ms and 120 ms, preferably between 20 ms and 50 ms.

It should also be noted that the concept "weight vector" used herein should not be interpreted to literally mean that this concept by necessity must be a vector. However, the concept in question refers to an entity which assigns different weights to different parts of the sensed signal.

It can also be observed that the number of delivered pulses necessary for determining the capture verification condition may vary. However, the number of delivered pulses must be sufficient such that there is a sufficient number of stored signals in each of the mentioned first and second groups. For example, it ought to be at least five or, more preferred, at least ten or, even more preferred, at least 20 stored signals in each of said first and second groups.

It is clear from the above that the capture verification condition in this case relates to an area within the time window. As mentioned above, such an area can be obtained by integrating the detected signal within the time window. However, the present invention is based on the insight that in a particular case some parts of the sensed signal within the time window can be more relevant than others for determining whether capture is the case. It has thus been found that by using a particular weight vector which assigns different weights to different parts of the sensed signal, an improved capture detection is obtained. It has also been found that such a particular weight vector can be determined on the basis of the signals stored in said first and second groups. The weight vector is thus chosen such that the signals in the first group is easily distinguished from the signals in the second group.

The mentioned weighted area is thus preferably an area determined by the sensed signal (for example the integral or negative integral of the sensed signal in said time window) but modified with the different assigned weights in accordance with the weight vector.

Preferably, the particular weight vector is determined such that by using the particular weight vector when calculating weighted areas for the stored signals, the signals in the first group are distinguished as much as possible, or at least to a high degree, from the signals in the second group. The weight vector can thus be determined such that the distinction between capture and loss of capture for a particular patient is as clear as possible.

According to one manner of carrying out the method, the method includes a Vario test in order to determine a capture threshold, wherein the stored signals are categorised as belonging to said first or second group based on the result of said Vario test. The Vario test is known to those skilled in the art. This is a method of determining the capture threshold. The Vario test is normally done by causing the pulse generator to automatically step through all possible pulse amplitude settings and by detecting (for example with the help of a surface electrocardiogram) at which amplitude the capture threshold is.

Preferably, the determination of said particular weight vector involves an iterative process. The iterative process can thereby involve assigning a weight vector and modifying said weight vector iteratively in order to arrive at said particular weight vector. By iteratively modifying the weight vector it is possible to arrive at a suitable or optimal weight vector in order to distinguish the signals in the first group from the signals in the second group.

The determination of said particular weight vector can be done by maximizing, or at least increasing to a sufficient level, a measure of how distinguished the signals in the first group are from the signals in said second group. This can be obtained by using a mathematical optimization method. Several different mathematical optimisation methods are known to those skilled in the art. Examples of such methods will be given below.

According to one manner of carrying out the method, the number of different parts of the signal within said time window, to which weights are assigned, is at least 8. Preferably, the first sensing circuit operates with a certain sampling frequency, and the number of different parts of the signal within the time window, to which weights are assigned, thereby corresponds to the sampling frequency. By using a sufficiently high number of different parts within the time window, a weight vector can be determined that clearly distinguishes the signals in the two groups from each other, i.e. a weight vector which is highly relevant for distinguishing capture from loss of capture.

According to one manner of carrying out the method, the control circuit and the first sensing electrode are arranged for unipolar sensing. It should be noted that the invention of course also is applicable to bipolar sensing.

The mentioned first heart chamber can be an atrium. It is often difficult to detect capture in an atrium. However, with the present invention it has been found that it is possible to determine a capture verification condition that can be used also for detecting capture in an atrium. The invention can of course also be used for detecting capture in a ventricle.

The heart stimulating system can be an implantable heart stimulating device in which said control circuit is contained, and the calculations performed in order to determine the particular weight vector can be performed in the implantable heart stimulating device. Alternatively, the calculations performed in order to determine the particular weight vector can be performed in a non-implantable unit that is separate from the implantable heart stimulating device. The mentioned non-implantable unit can be, for example, a so-called programmer that communicates via telemetry with an implanted heart stimulating device.

An implantable heart stimulating device according to the invention includes a control circuit that includes:

a pacing circuit adapted to be connected to a pacing electrode suited to be positioned in or at a heart chamber so as to receive pacing pulses from the pacing circuit such that the pacing circuit is able to pace the heart chamber, and a sensing circuit adapted to be connected to a sensing electrode, wherein said sensing electrode can be identical with or not identical with the pacing electrode, suited to be positioned in or at the heart chamber so as to transfer signals to the sensing circuit such that the sensing circuit is able to sense the heart chamber. The control circuit is arranged to be able to detect an evoked response to a pacing pulse delivered by the pacing circuit by sensing, with the sensing circuit, within a time window that follows after a pacing pulse delivered by the pacing circuit, wherein a sensed signal is categorized as a capture if one or more capture verification conditions are fulfilled. The device operates with at least one capture verification condition which is based on a calculated weighted area within the time window, wherein the weighted area is calculated by using a particular weight vector which assigns different weights for different parts of each sensed signal within said time window.

An implantable heart stimulating device according to the invention can thus use a capture verification condition that has been determined according to the method according to the invention. The particular weight vector used for calculating the weighted area can therefore be optimized for detecting capture in the particular patient in which the heart stimulating device has been implanted. With the implantable heart stimulating device according to the invention, capture can therefore be distinguished from loss of capture with high accuracy. The heart stimulating device can for example be used for detecting capture by unipolar sensing in an atrium. However, the implantable heart stimulating device can of course be set up to operate in other manners, for example for bipolar sensing. The implantable heart stimulating device can be arranged to detect capture either in an atrium or in a ventricle or in both an atrium and a ventricle. The implantable heart stimulating device can also be used in connection with bi-ventricular pacing.

An implantable heart stimulating system according to the invention includes:

an implantable heart stimulating device according to any of the above mentioned embodiments, and a first lead and the aforementioned first pacing electrode, wherein the first lead is connected to the aforementioned device and the first pacing electrode is arranged on the first lead.

According to a preferred embodiment of the system, the system also includes the aforementioned first sensing electrode.

The system according to the invention has advantages corresponding to those of the heart stimulating device according to the invention.

DESCRIPTION OF THE PREFERRED EMBODIMENTS

Figure 1:
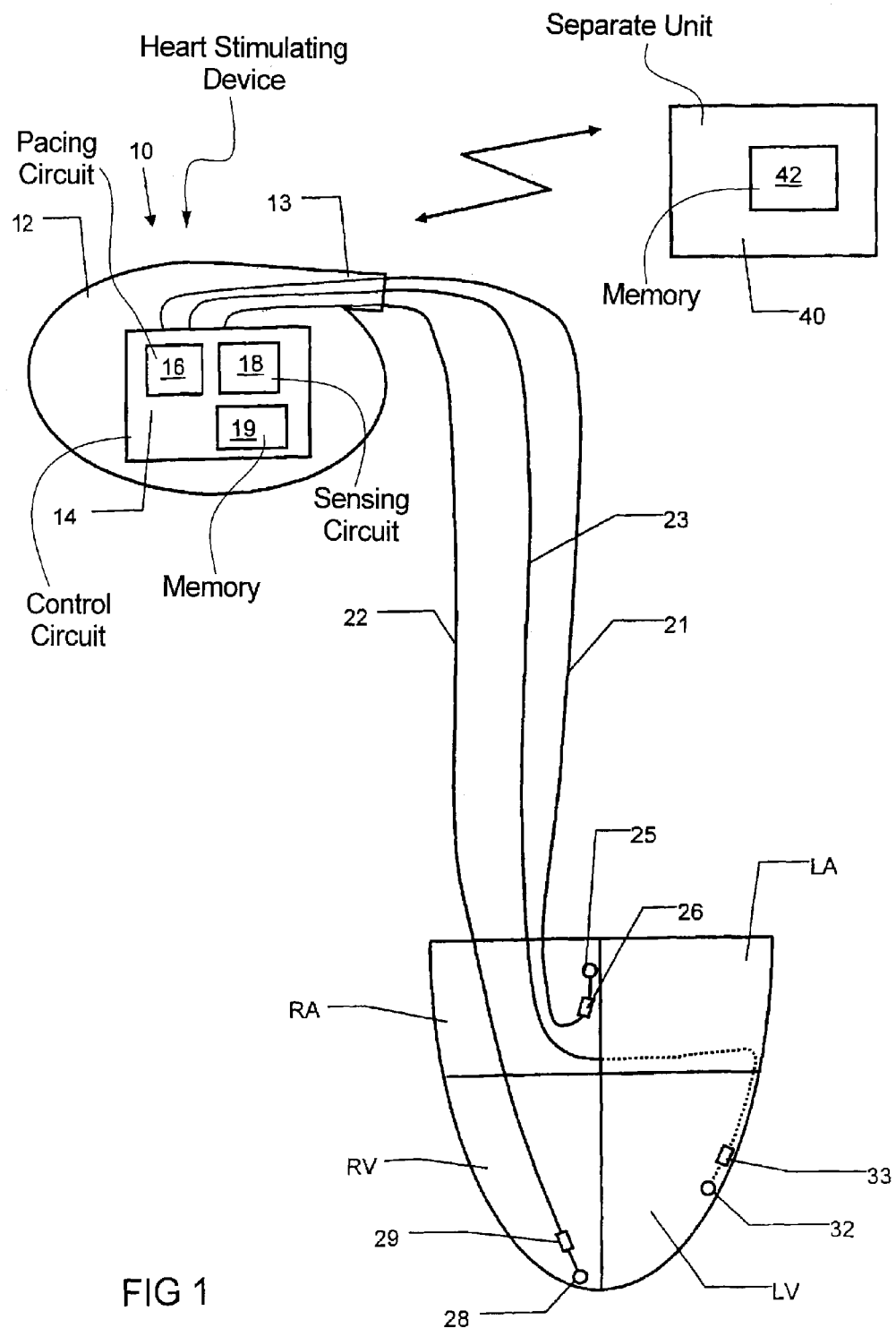
FIG. 1 shows schematically a heart stimulating system with a heart stimulating device connected to leads with sensing and pacing electrodes positioned in a heart. The figure also indicates a separate unit.

FIG. 1 shows schematically an embodiment of a heart stimulating system according to the invention. FIG. 1 also schematically shows a heart with a right ventricle RV, a left ventricle LV, a right atrium RA and a left atrium LA. The implantable heart stimulating system includes an implantable heart stimulating device 10 according to the invention and a first lead 21, a second lead 22 and a third lead 23. The implantable heart stimulating device 10 has a casing 12. Inside the casing 12 a control circuit 14 is located. The leads 21, 22, 23 are connected to the control circuit 14 via a connector portion 13 of the heart stimulating device 10. On the first lead 21, a first pacing electrode 25, 26 is arranged. In this case, the first pacing electrode 25, 26 is a bipolar electrode is formed by a tip electrode surface 25 and a ring electrode surface 26. The first pacing electrode 25, 26 can also function as a first sensing electrode 25, 26. In the shown embodiment, the first pacing and sensing electrode 25, 26 is located to pace and sense the right atrium RA.

In a corresponding manner, the second lead 22 has a second pacing and sensing electrode 28, 29. The second pacing and sensing electrode 28, 29 is in this case located in the right ventricle RV. The third lead 23 has a third pacing and sensing electrode 32, 33 arranged to pace and sense the left ventricle LV. In the shown embodiment, the electrodes are bipolar electrodes. However, it is also possible to operate the device 10 with unipolar pacing and sensing. In this case it is not necessary to have bipolar electrodes. In this case it is therefore sufficient with one electrode surface on each lead. In case of unipolar sensing, normally the casing 12 of the device 10 functions as a second electrode surface. As just described, the same electrode functions both for pacing and sensing. However, as is known to those skilled in the art, it is also possible that different electrodes (or electrode surfaces) are used for pacing and sensing.

The control circuit 14 has a first pacing circuit 16 adapted to be connected, via the first lead 21, to the first pacing electrode 25, 26 such that the first pacing circuit 16 is able to pace a first heart chamber, i.e. in this case the right atrium RA. The control circuit 14 also has first sensing circuit 18 adapted to be connected, via the first lead 21, to the first sensing electrode 25, 26 such that the first sensing circuit 18 is able to sense a first heart chamber, in this case the right atrium RA. The first sensing circuit 18 is in particular arranged to be able to sense an evoked response ER. Since those skilled in the art knows how such circuits as the pacing circuit 16 and the sensing circuit 18 are designed, these need not be described in more detail. The heart stimulating device 10 also includes a memory 19.

The control circuit 14 is thus able to detect an evoked response to a pacing pulse delivered by the first pacing circuit 16 by sensing, with the first sensing circuit 18, within a time window, i.e. the ER window, that follows after the delivery of a pacing pulse.

The control circuit 14 is also set up to categorize a sensed signal as an indication of a capture if one or more capture verification conditions are fulfilled. According to the present invention, at least one capture verification condition is based on a calculated weighted area A within the ER window. The weighted area A is calculated by using a particular weight vector which assigns different weights for different parts of the sensed signal within the ER window.

It can be noted that according to a preferred embodiment, the mentioned capture verification condition is the only capture verification condition which is used in the device 10. However, alternatively it is possible that this is one of a plurality of conditions used for deciding whether a sensed signal indicates capture. The mentioned capture verification condition can thus for example be combined with a slope and/or amplitude detection. According to a preferred embodiment, the device 10 according to the invention does not include any capture verification condition based on templates as in some of the above described documents.

FIG. 1 also indicates a separate unit 40. This separate unit 40 can be a so-called programmer that can communicate in a wireless manner (so-called telemetry) with an implanted device 10. The separate unit 40 includes a memory 42.

The present invention also concerns a method of determining a capture verification condition. Before describing this method in detail, some ideas behind the invention will be described.

Figure 2:
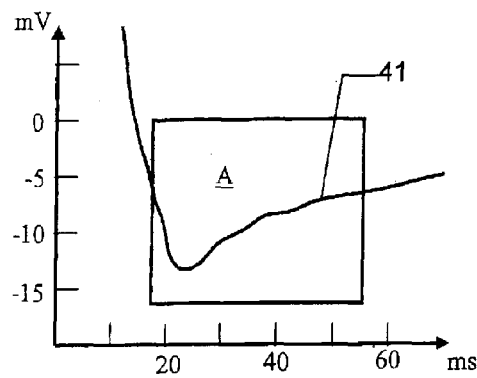
FIG. 2 shows schematically an example of a sensed signal within an evoked response window.

FIG. 2 shows schematically an ER window, marked as a rectangle, and a sensed signal 41. The vertical axis shows the amplitude and the horizontal axis shows the time. The signal 41 limits an area A in the ER window. The area A can for example be the negative integral of the sensed signal 41. The area A in this case is the area between 0 amplitude and the signal 41. However, it is possible to use alternative definitions of the area A. As already mentioned above, it is known that the area A can be used as a capture verification condition. For this discussion, it can be assumed that the signal 41 indicates capture.

Figure 3:
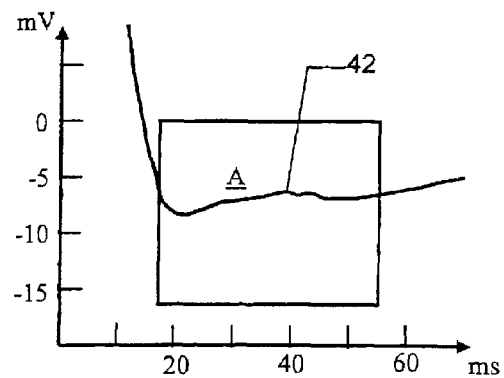
FIG. 3 shows another example of a sensed signal within an evoked response window.

FIG. 3 is similar to FIG. 2 but shows another sensed signal 42. For the sake of this discussion, it can be assumed that the signal 42 indicates loss of capture. The area A in FIG. 3 is smaller than the area A in FIG. 2. As is mentioned above, the area A can be used as a capture verification condition. However, sometimes it is difficult to distinguish capture from loss of capture by using such an area method. According to the present invention an improved capture verification condition can be determined.

Figure 7:
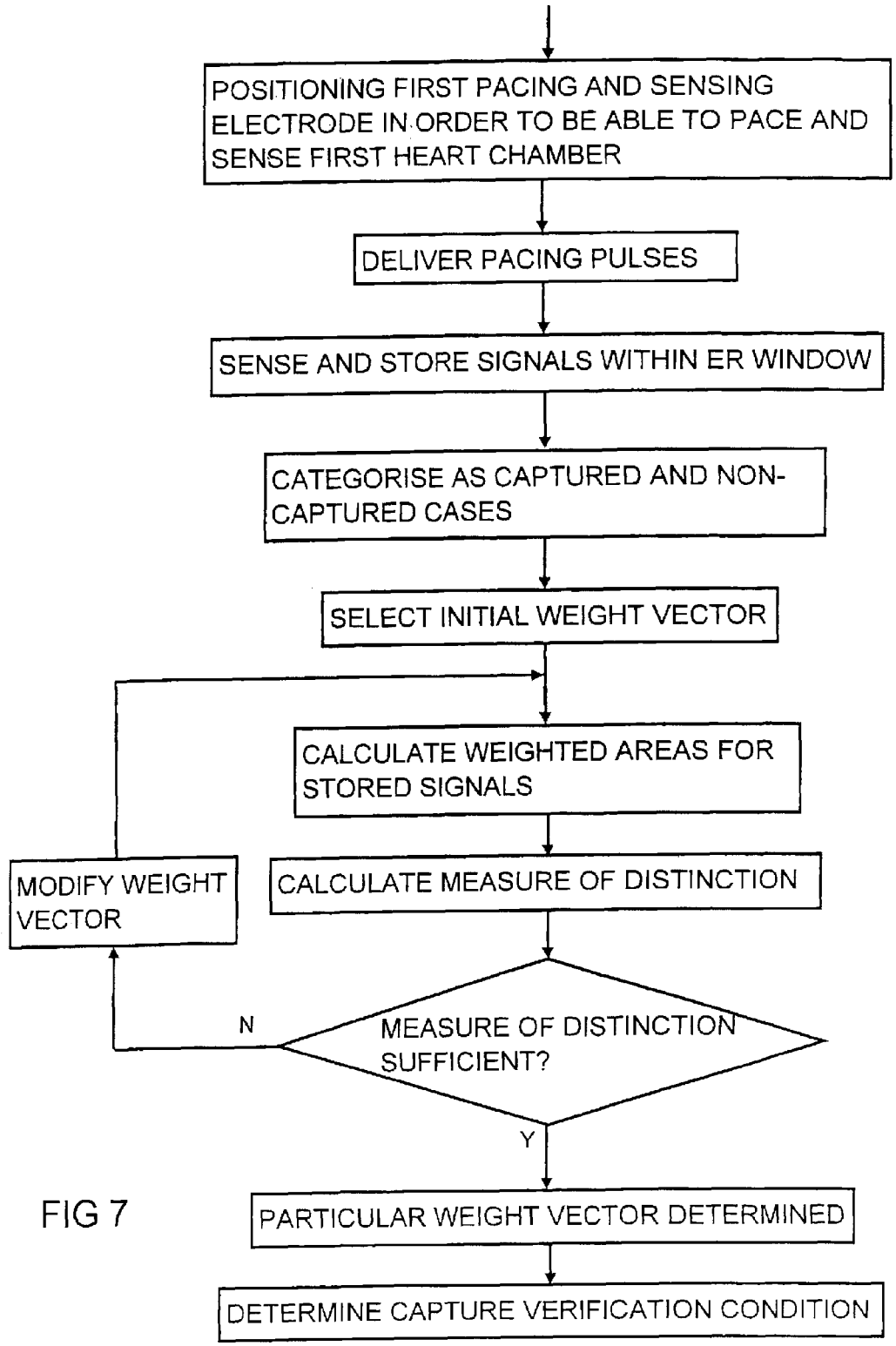
FIG. 7 shows schematically a flow chart for a method according to the invention.

FIG. 7 shows a schematic flow chart of a method according to the invention. A first pacing electrode 25 is positioned such that it is a able to deliver pacing pulses to a first heart chamber, for example to the right atrium RA. A first sensing electrode 25 is positioned such that it is able to sense evoked responses in response to pacing pulses delivered by the first pacing electrode 25. The first pacing electrode 25 can be the same as the first sensing electrode 25. The electrodes can preferably be connected to an implantable heart stimulating device 10 as described above. The whole system can thus be implanted in a patient.

At the next step, a number of pacing pulses are delivered via said first pacing electrode 25 to the first heart chamber RA. The delivery of the pacing pulses can involve a Vario test as described above. The delivered pacing pulses thus include both pulses which cause the heart chamber to capture and pulses which do not cause the heart chamber to capture.

After each delivered pacing pulse, signals from the first sensing electrode 25 is sensed within the ER window. The sensed signals are stored in a memory 19, 42. Based on the Vario test, the sensed signals can be categorised in a first group and in a second group. The first group represents captured cases and the second group represents non-captured cases.

Based on the stored signals, a particular weight vector which assigns different weights for different parts of each sensed signal within said ER window is determined. The weight vector is to be used for calculating a weighted area within the ER window. The particular weight vector can be determined by an iterative process, for example as schematically illustrated in FIG. 7.

First an initial weight vector is selected. The selected initial weight vector may for example be a weight vector that assigns the same weight to all the different parts of the signal within the ER window. Another example of an initial weight vector that can be used is a weight vector where the weight $x_i$ associated with a certain sample (or part of the ER window) i is selected as $As_{iC}$-$As_{iL}$, where $As_{iC}$ is the average of the values of sample i for the captured cases, i.e. for the stored signals in the first group, and $As_{iL}$ is the average of the values of sample i for the loss cases, i.e. for the stored signals in the second group.

The number of different parts of the ER window to which different weights can be assigned can for example correspond to the sampling frequency of the device. If for example the sampling frequency is 512 Hz and if the ER window is 50 ms long, the number of different parts within the ER window is about 25. The weighted area for a sensed signal can be calculated as follows.

$$A_W = \sum_{i=1}^{N} x_i \cdot s_i$$

where $A_W$ is the weighted area, $x_i$ is the weight associated with the sample i, $s_i$ is the ith sample and N is the number of samples in the window (i.e. the number of different parts in the ER window to which different weights can be assigned). The weighted areas are calculated for the stored signals with the help of the selected weight vector.

Next a measure of how distinguished the signals in the first group are from the signals in the second group is calculated. For the sake of simplicity, this measure is below called "measure of distinction".

Figure 4:
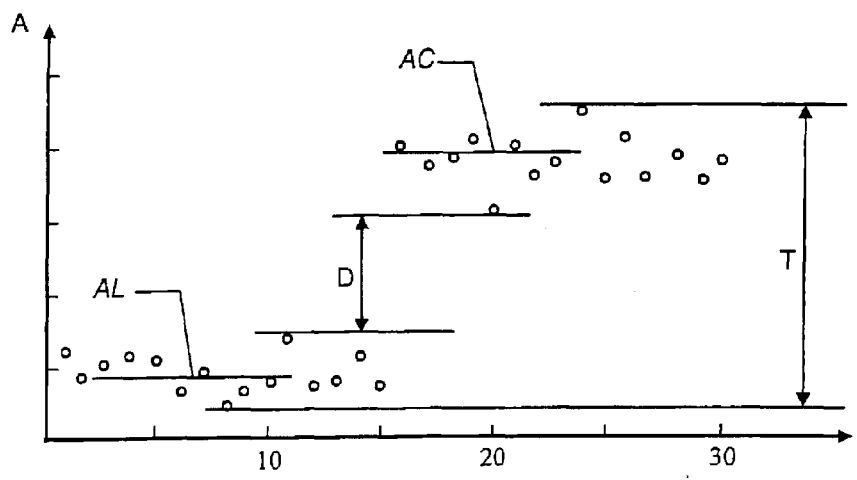
FIG. 4 shows schematically different areas measured for a number of signals representing captured and non-captured cases.

Reference is now made to FIG. 4. FIG. 4 shows the areas A calculated with a particular weight vector for the different stored signals, indicated with small circles. The horizontal axis indicates the number of different stored signals. According to this schematic example only 30 signals are stored. The first 15 stored signals represent non-captured beats and the following 15 stored signals represent captured beats. The first 15 signals are thus the mentioned second group of stored signals and the following 15 signals are the mentioned first group of signals. In FIG. 4 the difference D represents the smallest difference in weighted area between the signals indicating non-capture and the signals indicating capture. The difference T indicates the largest difference in weighted area between the signals indicating non-capture and the signals indicating capture. The relationship D/T is one possible measure of how distinguished the signals in the first group are from the signals in the second group. However, the relationship D/T is only one example of a measure of distinction. Another example of a measure of distinction is the following:

$$M = \left| \frac{AC - AL}{\sqrt{\frac{SC}{NC} + \frac{SL}{NL}}} \right|$$

where M is a measure of distinction,

AC is the average of the calculated weighted areas for the captured beats, i.e. for the mentioned first group, AL is the average of the calculated weighted areas for the loss beats, i.e. for the mentioned second group, SC is the standard deviation for the calculated weighted areas for the captured beats, i.e. for the mentioned first group, NC is the number of capture beats, i.e. the number of stored signals in the first group, SL is the standard deviation for the calculated weighted areas for the loss beats, i.e. for the mentioned second group, and NL is the number of loss beats, i.e. the number of stored signals in the second group. Approximate levels for AC and AL are shown in FIG. 4.

Returning to FIG. 7, the iteration continues by modifying the weight vector. Thereafter weighted areas are calculated for the stored signals with the modified weight vector. The measure of distinction is calculated again. The iteration process continues until a suitable weight vector has been found. The iteration can for example continue until a maximum has been found for the measure of distinction, or until the measure of distinction is sufficient.

The particular weight vector has now been determined. The capture verification condition, based on this particular weight vector, is then determined.

It should be observed that FIG. 7 only very schematically shows an iterative process. The iterative process can be any well known suitable mathematical optimization method. One such method is Rosenbrock's method. Other methods can also be used, such as Powell's method, the Simplex method or a Fibonacci search.

Figure 8:
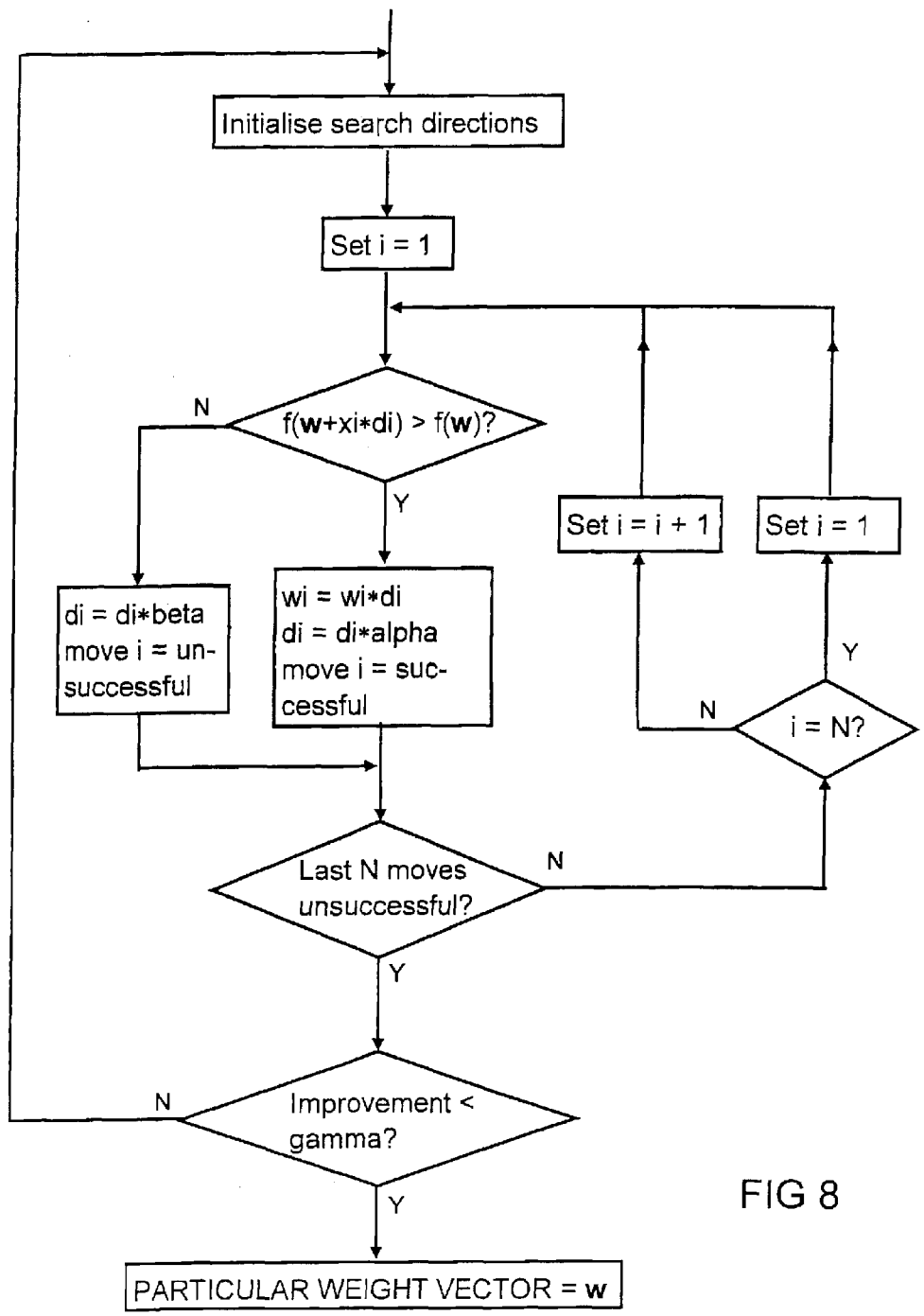
FIG. 8 shows a flow chart of an iterative process that can be used in the method according to the invention.

FIG. 8 shows in some more detail than in FIG. 7 an example of an iterative process that can be used in order to determine the particular weight vector. The process of FIG. 8 is a version of Rosenbrock's method applied to the present case. The following symbols are used in FIG. 8.

w is the weight vector (which contains N elements),
wi is weight number i (the ith element in w),
x is a set of search directions,
xi is search direction i,
di is the step size in search direction i,
f(w) is a "measure of distinction" (for example D/T or M) for the weight vector w,
alpha is a constant, wherein alpha>1,
beta is a constant, wherein −1<beta<0,
gamma is a constant that implicitly controls the number of iterations.

As can be seen in FIG. 8, first a search direction is initialized. The process is such that all search directions will be searched until a move in any direction would generate a lower value of distinction. Then i is set to be equal to 1. Next f is calculated for a modified w (modified in search direction xi), i.e. f(w+xi*di) is calculated. If the calculated f(w+xi*di)>f(w), then the move to the modified w is considered to be successful. wi is then set to be equal to wi*di and di is set to di*alpha. The process then continues to the next step below in FIG. 8. If it is not the case that f(w+xi*di)>f(w), then the move is considered to be unsuccessful and the search direction di is changed to di*beta.

At the step below it is checked whether the last N moves were considered unsuccessful. If this is not the case, then, if i is not equal to N, i is increased to i+1 and the process continues as shown by the arrows. If i is equal to N, then i is set to be equal to 1 before the process continues.

If, instead, it is found that the last N moves were unsuccessful, it is at the next step checked whether the improvement (i.e. the increase in f(w)) is less than gamma. Gamma can be a predetermined small value. If the improvement is under this predetermined value, it is assumed that further iterations will not lead to any significant improvement. The particular weight vector is thus determined as the w that is obtained through the iteration.

If instead that improvement is not less than gamma, the iteration continues as shown in FIG. 8.

By the iterative process described in connection with FIGS. 7 and 8 a particular weight vector is thus determined. The particular weight vector is such that by using the particular weight vector and calculating weighted areas for the stored signals, the signals in the first group are distinguished as much as possible, or at least to a high degree, from the signals in the second group. The capture verification condition is thus determined as whether the weighted area, calculated with the particular weight vector that has been found by the iterative process, of a sense signal within an ER window is above or below a certain value.

Figure 5:
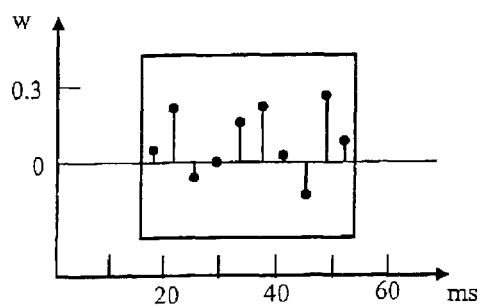
FIG. 5 illustrates schematically different weight values of a weight vector for different parts of an evoked response window.
Figure 6:
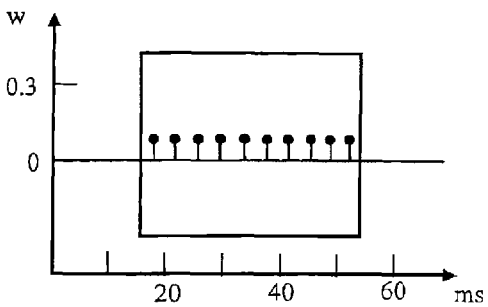
FIG. 6 shows schematically another example of weight values of a weight vector within the evoked response window.

FIG. 5 illustrates schematically the weights w of a weight vector for different parts of the ER window. For simplicity, it is assumed that different weights are assigned only to 10 different parts of a sensed signal within the ER window. As a comparison, FIG. 6 shows schematically the weights of a weight vector that does not assign different weights to different parts of the signal within the ER window. In this case the weight of each of the ten parts of the signal within the ER window is thus equal to 0.1 (1/N in the above equation). A weight vector of the kind shown in FIG. 6 thus corresponds to the normal integration method according to the prior art that does not assign different weights to different parts of the signal.

With the particular weight vector determined in accordance with the present invention, the signals of the first group are thus more easily distinguished from the signals in the second group than if the signals in the first and second groups were distinguished from each other by the area method without assigning different weights to different parts of the sensed signal within the ER window. By finding an optimized weight vector, the ratio D/T or M (or another measure of distinction) thus increases. When later using the determined capture verification condition in a heart stimulating device 10, capture can be detected with higher accuracy than before.

The calculations necessary in order to determine the particular weight vector is preferably done in a non-implantable unit 40 that is separate from the implantable heart stimulating device 10. The calculations can thus be done in a so-called programmer 40. Alternatively, it is possible to perform the calculation in the implantable heart stimulating device 10 itself. The capture verification condition can be determined directly after implant of the heart stimulating device 10 in a patient. Alternatively, or additionally, the capture verification condition can be determined when the heart stimulating device 10 has been implanted for a certain time. It is also possible to determine a capture verification condition for an implanted heart stimulating device 10 several times, since it is possible that for example the polarisation conditions for the electrodes 25, 26 may change over time. It can therefore be beneficial to at a later time determine a new capture verification condition with the method according to the invention in order to optimize the capture verification of the implanted heart stimulating device 10.

A heart stimulating device 10 according to the invention thus uses a particular weight vector for calculating a weighted area in an ER signal. The weight vector used in the device 10 is such that the different weights assigned by the weight vector for different parts of the sensed signal within the ER window are optimized for distinguishing capture from loss of capture with the help of the weighted areas. Although above it has been exemplified that the device according to the invention is used for unipolar sensing of an atrium, the device can also be used for sensing any other chamber of the heart and also for bipolar sensing.

The invention is not limited to the described embodiments but may be varied and modified within the scope of the following claims. In can also be noted that for simplicity, at certain locations herein only the reference RA is used for a heart chamber and only the reference numerals 25, 26 are used for the electrodes. As explained above, however, the present invention is applicable to any of the chambers of the heart.

Although modifications and changes may be suggested by those skilled in the art, it is the invention of the inventor to embody within the patent warranted heron all changes and modifications as reasonably and properly come within the scope of his contribution to the art.

I claim:

1. A method for determining a capture verification condition for a heart stimulating system, said heart stimulating system comprising a control circuit, a pacing electrode, a sensing electrode, a pacing circuit electrically connected to the pacing electrode, and a sensing circuit electrically connected to the sensing electrode, said method comprising the steps of:

positioning said pacing electrode to allow said pacing electrode to deliver pacing pulses in vivo to a heart chamber;

positioning said sensing electrode to allow said sensing electrode to sense evoked response in vivo produced in response to said pacing pulses delivered by said pacing electrode;

delivering a plurality of pacing pulses via said pacing electrode to said heart chamber, said plurality of pacing pulses including pulses causing said heart chamber to capture and pulses which do not cause said heart chamber to capture;

sensing signals in said sensing circuitry, as sensed signals, via said sensing electrode within a time window following each of said plurality of delivered pacing pulses, and storing the sensed signals in a memory;

automatically electronically categorizing the stored signals in a first group, representing captured cases, and a second group, representing non-captured cases;

based on said stored signals, automatically electronically determining a weight vector that assigns different weights to different parts of each sensed signal within said time window, and automatically electronically calculating a weighted area within said time window by applying said weight vector to the signals in said first group and the signals in said second group, said weight vector causing a greater distinction between the signals in said first group and the signals in said second group than would exist without said weight vector; and automatically electronically determining a capture verification condition by determining whether said weighted area of a sensed signal within said time window is above or below a predetermined value.

2. A method as claimed in claim 1 comprising automatically electronically calculating said weighted area as an area defined by a sensed signal modified with differently assigned weights according to said weight vector.

3. A method as claimed in claim 1 comprising automatically electronically determining said weight vector to maximize distinguishment between signals in said first group from signals in said second group.

4. A method as claimed in claim 1 comprising executing a Vario test to determine a capture threshold, and categorizing said stored signals as being in said first group or in said second group depending on said Vario test.

5. A method as claimed in claim 1 comprising automatically electronically determining said weigh vector in an iterative procedure.

6. A method as claimed in claim 5 comprising, in said iterative procedure, determining an initial weight vector and modifying said initial weight vector iteratively to produce said weight vector.

7. A method as claimed in claim 1 comprising determining said weight vector by maximizing a measure representing a degree of distinguishment between signals in said first group from signals in said second group.

8. A method as claimed in claim 1 comprising determining said weight vector using a mathematical optimization technique.

9. A method as claimed in claim 1 comprising assigning respectively different weights for at least eight different parts of each sensed signal within said time window.

10. A method as claimed in claim 9 comprising operating said sensing circuit at a sampling frequency and using, as said number of different parts of said signal within said time window, a number corresponding to said sampling frequency.

11. A method as claimed in claim 1 comprising operating said control circuit and said sensing electrode for unipolar sensing.

12. A method as claimed in claim 1 comprising positioning said pacing electrode in an atrium, as said heart chamber.

13. A method as claimed in claim 1 wherein said heart stimulating system comprises an implantable heart stimulating device that contains said control circuit therein, and comprising performing calculations to determine said weight vector inside said implantable heart stimulating device.

14. A method as claimed in claim 1 wherein said heart stimulating system comprises an implantable heart stimulating device containing said control circuit therein, and comprising performing calculations to determine said particular weight vector in a non-implantable unit that is separate from, and communicates with, said implantable heart stimulating device.

15. An implantable heart stimulating device for determining a capture verification condition for a heart comprising:

a pacing electrode positioned to allow said pacing electrode to deliver pacing pulses in vivo to a heart chamber;

a sensing electrode positioned to allow said sensing electrode to sense evoked response in vivo produced in response to said pacing pulses delivered by said pacing electrode;

a control circuit connected to said pacing electrode that controls delivery of a plurality of pacing pulses via said pacing electrode to said heart chamber, said plurality of pacing pulses including pulses causing said heart chamber to capture and pulses which do not cause said heart chamber to capture;

sensing circuitry connected to said sensing electrode to sense signals, as sensed signals, via said sensing electrode within a time window following each of said plurality of delivered pacing pulses, a memory in communication with said sensing circuitry in which the sensed signals are stored;

said control circuit automatically categorizing the stored signals in a first group, representing captured cases, and a second group, representing non-captured cases, and based on said stored signals, automatically determining a weight vector that assigns different weights to different parts of each sensed signal within said time window, and automatically calculating a weighted area 25 within said time window by applying said weight vector to the signals in said first group and the signals in said second group, said weight vector causing a greater distinction between the signals in said first group and the signals in said second group than would exist without said weight vector, and automatically 30 determining a capture verification condition by determining whether said weighted area of a sensed signal within said time window is above or below a predetermined value.

16. An implantable heart stimulating device as claimed in claim 15 wherein said control circuit automatically calculates said weighted area as an area defined by a sensed signal modified with differently assigned weights according to said weight vector.

17. An implantable heart stimulating device as claimed in claim 15 wherein said control circuit automatically determines said weight vector to maximize distinguishment between signals in said first group from signals in said second group.

18. An implantable heart stimulating device as claimed in claim 15 wherein said control circuit executes a Vario test to determine a capture threshold, and categorizing said stored signals as being in said first group or in said second group depending on said Vario test.

19. An implantable heart stimulating device as claimed in claim 15 wherein said control circuit automatically determines said weigh vector in an iterative procedure.

20. An implantable heart stimulating device as claimed in claim 15 wherein said control circuit, in said iterative procedure, determines an initial weight vector and modifies said initial weight vector iteratively to produce said weight vector.

21. An implantable heart stimulating device as claimed in claim 15 wherein said control circuit determines said weight vector by maximizing a measure representing a degree of distinguishment between signals in said first group from signals in said second group.

22. An implantable heart stimulating device as claimed in claim 15 wherein said control circuit determines said weight vector using a mathematical optimization technique.

23. An implantable heart stimulating device as claimed in claim 15 wherein said control circuit assigns respectively different weights for at least eight different parts of each sensed signal within said time window.

24. An implantable heart stimulating device as claimed in claim 15 wherein said control circuit operates said sensing circuit at a sampling frequency and using, as said number of different parts of said signal within said time window, a number corresponding to said sampling frequency.

25. An implantable heart stimulating device as claimed in claim 15 wherein said control circuit operates said control circuit and said sensing electrode are configures for unipolar sensing.

26. An implantable heart stimulating device as claimed in claim 15 wherein said control circuit said pacing electrode as configured for placement in an atrium, as said heart chamber.

27. An implantable heart stimulating system comprising:
an electrode lead carrying a pacing electrode positioned to allow said pacing electrode to deliver pacing pulses in vivo to a heart chamber, and a sensing electrode positioned to allow said sensing electrode to sense evoked response in vivo produced in response to said pacing pulses delivered by said pacing electrode;
a control circuit connected to said pacing electrode via said electrode lead, that controls delivery of a plurality of pacing pulses via said pacing electrode to said heart chamber, said plurality of pacing pulses including pulses causing said heart chamber to capture and pulses which do not cause said heart chamber to capture;
sensing circuitry connected to said sensing electrode via said electrode lead to sense signals, as sensed signals, via said sensing electrode within a time window following each of said plurality of delivered pacing pulses,
a memory in communication with said sensing circuitry in which the sensed signals are stored;
said control circuit automatically categorizing the stored signals in a first group, representing captured cases, and a second group, representing non-captured cases, and based on said stored signals, automatically determining a weight vector that assigns different weights to different parts of each sensed signal within said time window, and automatically calculating a weighted area within said time window by applying said weight vector to the signals in said first group and the signals in said second group, said weight vector causing a greater distinction between the signals in said first group and the signals in said second group than would exist without said weight vector, and automatically determining a capture verification condition by determining whether said weighted area of a sensed signal within said time window is above or below a predetermined value.

28. An implantable heart stimulating system as claimed in claim 27 wherein said sensing electrode is also carried by said lead.

* * * * *